(12) United States Patent
Pennie

(10) Patent No.: US 10,300,481 B2
(45) Date of Patent: May 28, 2019

(54) CENTRIFUGE TUBE ASSEMBLY FOR SEPARATING, CONCENTRATING AND ASPIRATING CONSTITUENTS OF A FLUID PRODUCT

(71) Applicant: Patrick Pennie, Fort Meyers, FL (US)

(72) Inventor: Patrick Pennie, Fort Meyers, FL (US)

(*) Notice: Subject to any disclaimer, the term of this patent is extended or adjusted under 35 U.S.C. 154(b) by 443 days.

(21) Appl. No.: 14/741,920

(22) Filed: Jun. 17, 2015

(65) Prior Publication Data
US 2016/0367982 A1 Dec. 22, 2016

(51) Int. Cl.
*B01L 1/00* (2006.01)
*B01L 3/00* (2006.01)

(52) U.S. Cl.
CPC ..... *B01L 3/5021* (2013.01); *B01L 2200/0684* (2013.01); *B01L 2200/0689* (2013.01); *B01L 2200/141* (2013.01); *B01L 2300/0681* (2013.01); *B01L 2300/0832* (2013.01); *B01L 2400/0409* (2013.01); *B01L 2400/0478* (2013.01)

(58) Field of Classification Search
None
See application file for complete search history.

(56) References Cited

U.S. PATENT DOCUMENTS

| 4,057,050 A | * | 11/1977 | Sarstedt | A61B 5/15003 |
| | | | | 222/386 |
| 2005/0065454 A1 | * | 3/2005 | Manoussakis | B01L 3/50825 |
| | | | | 600/576 |

* cited by examiner

*Primary Examiner* — Jyoti Nagpaul
(74) *Attorney, Agent, or Firm* — William E. Noonan

(57) ABSTRACT

A centrifuge tube assembly includes an elongate tubular receptacle having upper and lower ends and a side wall that extends between the ends. A cap attached to the receptacle carries a common inlet/outlet port formed therethrough for communication with an interior chamber of the tubular receptacle. A liquid impermeable piston is longitudinally movable through the receptacle chamber and sealably interengages an interior wall of the receptacle. The piston separates upper and lower regions of the chamber, which respectively communicate with the inlet/outlet port and a pressure neutralizing vent. Biological products are introduced into and aspirated from the receptacle through the inlet/outlet port.

14 Claims, 6 Drawing Sheets

CENTRIFUGE TUBE ASSEMBLY FOR SEPARATING, CONCENTRATING AND ASPIRATING CONSTITUENTS OF A FLUID PRODUCT

FIELD OF THE INVENTION

This invention relates to a centrifuge tube, that enables fluid biological products such as blood, stem cells, bone marrow aspirate and the like to be effectively separated and concentrated into constituent components, which may be conveniently aspirated after the biological product has been centrifuged. The apparatus is particularly effective for sequestering platelet-rich plasma and bone marrow aspirate for use in surgical, medical and veterinary procedures.

BACKGROUND OF THE INVENTION

Platelet-rich blood plasma is required for use in various medical procedures. This blood product is particularly effective due to its growth promoting features, which assist greatly in wound healing and bone regeneration. Presently, blood plasma with a high concentration of platelets is utilized for dental implants and other periodontal procedures, facial reconstruction, oral or maxillofacial surgery and chronic wound care. In order to obtain a required concentration of platelets, a blood sample normally must be centrifuged in order to separate the blood into its component blood products (i.e. plasma, red blood cells and platelets). The platelets, typically in a form of a white "buffy coat", are then separated from the blood sample and sequestered in concentrated form through aspiration. Conventional aspiration techniques often fail to provide a satisfactory concentration of platelets. Cross-contamination between the constituent products is frequently encountered. We have determined that the need exists for a cost effective apparatus that facilitates the sequestration of platelets while minimizing cross-contamination between blood components.

The centrifuge tube assemblies disclosed in U.S. Pat. Nos. 6,835,353 and 7,976,796 were developed to address the foregoing concerns. Those devices employ various arrangements of aspiration pipes, which are incorporated into the centrifuge tube. Although these products achieve superior results and have proven to constitute a significant improvement over the prior art, I have determined that the need exists for an even simpler, more efficient and more reliable design.

An improved centrifuge tube is needed for separating and aspirating a host of biological products, including but not limited to blood products, bodily fluids, stem cells, bone marrow aspirate, etc. for use in both medical and veterinary applications. It is important for such products to be separated and concentrated into constituent components quickly, effectively and without causing cross-contamination of those components.

SUMMARY OF THE INVENTION

It is therefore an object of the present invention to provide a simpler, more efficient and yet highly reliable centrifuge tube that enables blood, bone marrow aspirate and other fluid biological products to be effectively separated and concentrated into constituent components and conveniently aspirated following separation.

It is a further object of this invention to provide a centrifuge tube with aspirating capabilities that is manufactured much less intricately and far less expensively than existing devices of this type.

It is a further object of this invention to provide an aspirating centrifuge tube that is extremely simple to operate.

It is a further object of this invention to provide a centrifuge tube that permits a host of chemicals, bodily fluids and other biological products to be separated and individually aspirated with minimal cross-contamination.

It is a further object of this invention to provide a centrifuge tube assembly that minimizes potential contamination of biological liquids while such liquids are injected into and aspirated from the tube.

It is a further object of this invention to provide a centrifuge tube device that features an improved, secure cover that maintains sterility of the centrifuged fluids, prevents aerosolization and eliminates the need to use centrifugal bucket caps.

It is a further object of this invention to provide a centrifuge tube assembly that eliminates the use of aspirating tubes entirety so that manufacturing complexity and costs are reduced and more volume is made available in the tube for accommodating fluids.

It is a further object of this invention to provide a centrifuge tube assembly that facilitates aspiration by eliminating aspiration pipes, which are subject to kinking and malfunction.

It is a further object of this invention to provide a centrifuge tube that is particularly effective for sequestering a high concentration of platelet-rich plasma for use in various medical, surgical and veterinary procedures.

It is a further object of this invention to provide an aspirating centrifuge tube that may be used effectively for separating and aspirating a wide range of biological products, including but limited to blood, stem cells, bone marrow aspirate, etc.

It is a further object of this invention to provide a centrifuge tube that may be used effectively in various medical and veterinary applications.

This invention features a centrifuge tube assembly preferably in the form of an elongate tubular receptacle. The receptacle may include an opposite upper and lower ends and a side wall that extends between the upper and lower end walls. A cap engages the side wall and extends across the upper end of the receptacle. A common inlet and outlet port is formed through the cap in communication with an interior chamber of the tubular receptacle. A liquid impermeable diaphragm or piston is mounted within the chamber of the tubular receptacle for sealably engaging the interior surface of the side wall of the receptacle and sliding longitudinally through the receptacle. Blood product or other biological fluid is introduced through the inlet/outlet port into a region of the chamber between the piston and the upper end of the receptacle. The piston is driven downwardly through the tubular receptacle as the fluid is introduced. The tube device is centrifuged to separate the fluid into constituent components. One or more layers of the separated fluid may then be conveniently aspirated through the common inlet/outlet port. A vent is formed through the lower end of the receptacle for equalizing or neutralizing air pressure in the receptacle chamber when either fluid is introduced into the chamber or constituent components are aspirated from the chamber.

In a preferred embodiment, the cap is removably connected to the side wall of the tubular receptacle. The opposite, lower end of the tubular receptacle may include an annular base for supporting the tubular receptacle to extend upwardly from an underlying surface.

The piston may be slidable longitudinally within the tubular receptacle while maintaining peripheral sealing engagement with the interior wall of the tubular receptacle. The piston may carry an annular O-ring that sealably interengages the interior surface of the side wall.

The cap may include a tapered or conical channel that communicates with the common inlet and outlet port for facilitating aspiration of the one or more fluid layers therethrough. The vent may carry a filter for restricting the entry of contaminants into the chamber through the vent.

A method of separating fluid biological product into constituent components using the foregoing assembly is also featured. Initially, a blood sample or other fluid biological product is introduced into the tubular receptacle formed through the common inlet/outlet port. As biological product is introduced into the tubular receptacle, it pushes the sealing piston downwardly within the tubular receptacle against the neutral air pressure of a vented region of the receptacle chamber formed between the piston and the lower end wall of the receptacle. When the receptacle is filled with a fluid biological product to a desired level, the inlet/outlet port is closed and the assembly is centrifuged to separate the fluid product into constituent components. The inlet/outlet port is then opened and one or more of the constituent components are aspirated through the inlet/outlet port. Once again, the vent provides for neutral pressurization within the receptacle so that aspiration is facilitated. As successive layers of constituent components are removed from the centrifuge tube, air is pulled into the receptacle through the vent and the piston is drawn upwardly through the tubular receptacle.

BRIEF DESCRIPTION OF THE DRAWINGS

Other objects, features and advantages will occur from the following description of a preferred embodiment and the accompanying drawings, in which.

DETAILED DESCRIPTION OF PREFERRED EMBODIMENTS

Figure 1:
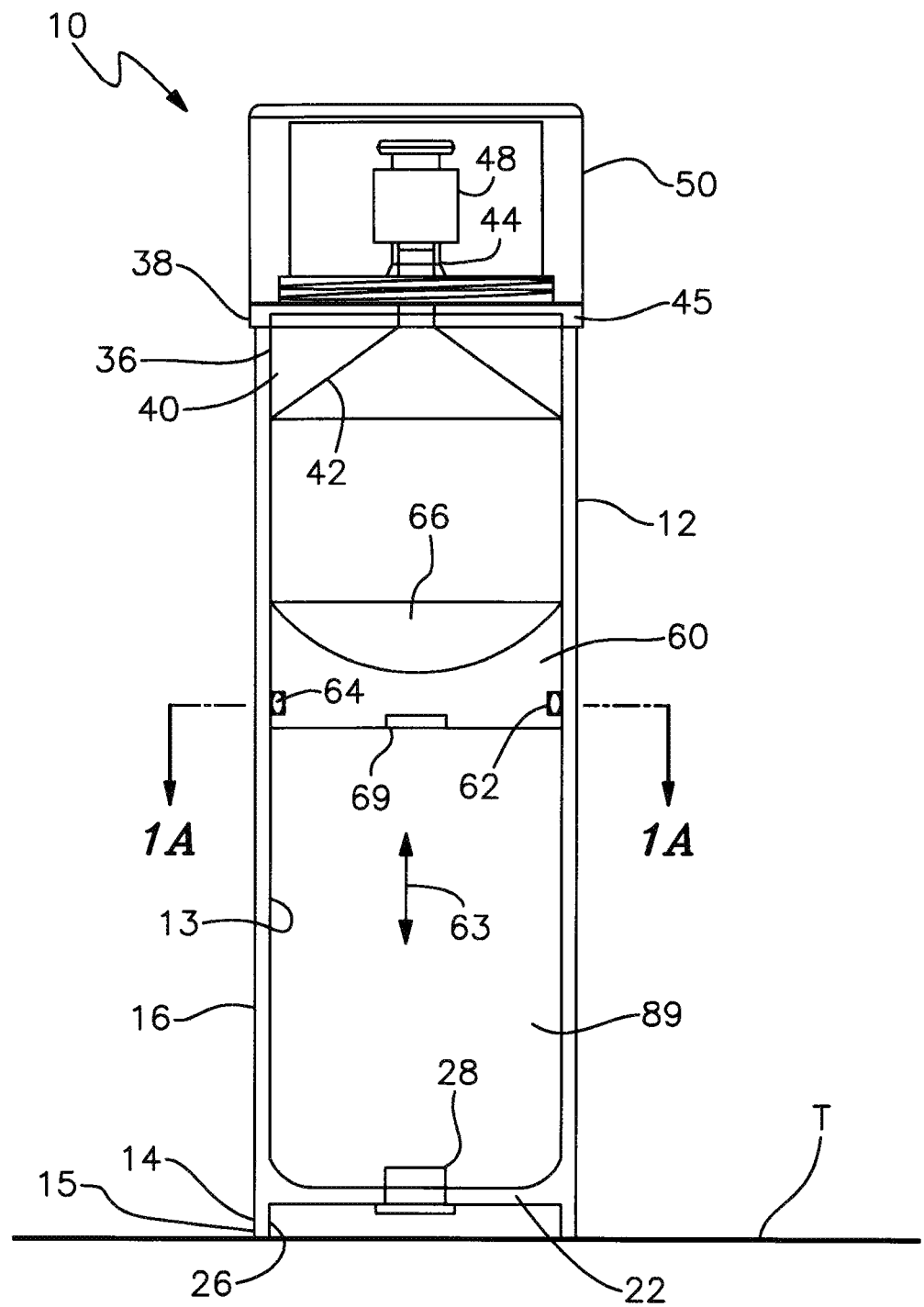
FIG. 1 is an elevational cross sectional view of a preferred embodiment of the centrifuge tube assembly of this invention without any fluid or other biological product within the tubular receptacle.

There is shown in FIG. 1 a centrifuge tube assembly 10 that includes a tubular or cylindrical receptacle 12 having an open upper end and an opposite lower end 14. A cylindrical side wall 16 extends between lower end 14 and upper end 13. Tubular receptacle 12 further includes an interior chamber 18 that extends from lower end 14 to upper end 13. This chamber accommodates blood, chemicals, stem cells, bone marrow aspirate or other biological fluids/products to be centrifuged and aspirated using assembly 10.

As used herein, "centrifuge tube" should be understood to comprise various shapes and sizes of vessels, receptacles and containers having an interior chamber for holding a fluid biological product and capable of being centrifuged to separate the product into constituent components. The centrifuge tube is not limited to just tubular and elongate configurations, although such configurations will typically be used in preferred embodiments of the invention.

Figure 2:
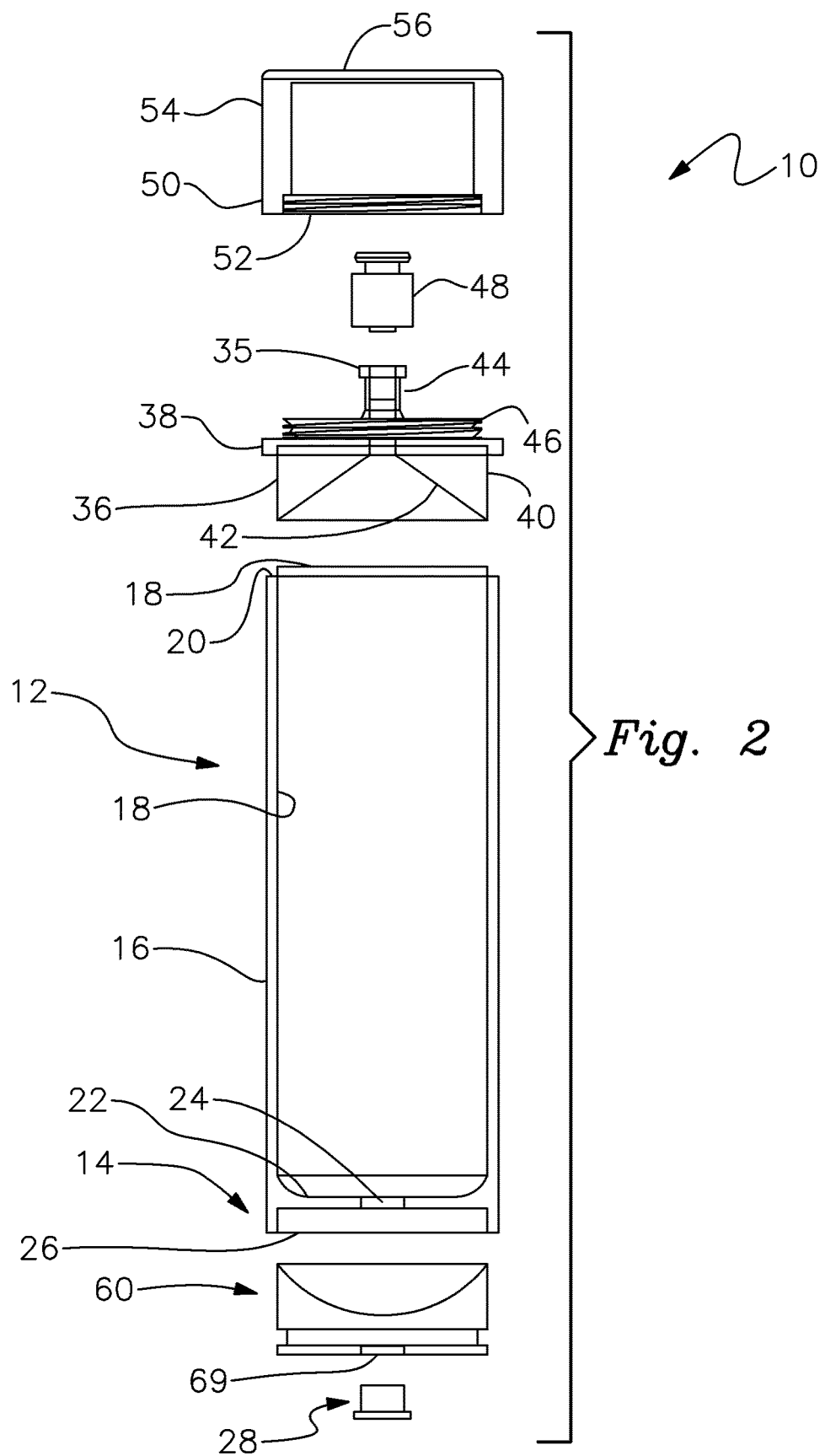
FIG. 2 is an exploded view of the assembly depicting the individual components of the preferred device.

As best shown in FIG. 2, an annular notch 20 is formed at the upper end 13 of side wall 16. This notch enables an upper end cap 36 to securely and sealably interengage receptacle 12 as will be further described below. Lower end 14 of receptacle 12 includes a floor 22 that defines the bottom of interior chamber 18. An annular base 15 is connected unitarily with and depends from receptacle floor 22 and side wall 16. The annular base stably supports the tubular receptacle in an upright condition on a table or other flat or horizontal surface. In this way, the centrifuge tube assembly does not require a separate rack or holder for support. Annular base 15 also securely supports the device 10 upright in a standard centrifuge machine in accordance with the orientation depicted in FIGS. 1 and 5.

Tubular receptacle 12 is typically composed of a durable plastic material such as polypropylene or other material suitable for medical or veterinary applications. The tube should also be constructed to withstand the forces exerted by centrifuging. In certain applications, shatter resistant glass may be employed.

A plurality of graduated volume markings, not shown herein but see U.S. Pat. No. 7,976,796, may be formed at various selected intervals along the exterior side wall of tubular receptacle 12. Such markings should be formed at heights or intervals corresponding to commonly selected volumes of biological product that will be introduced into the tube. Such markings may be varied within the scope of this invention.

Figure 3:
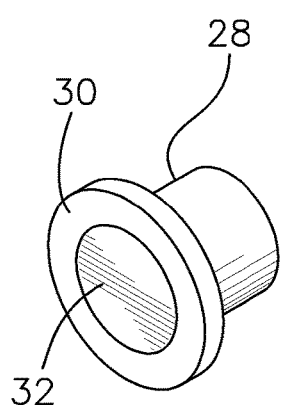
FIG. 3 is a perspective view of a vent element and filter used in the assembly.
Figure 3A:
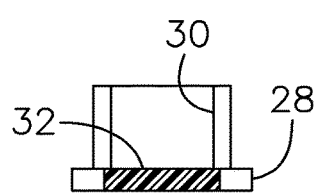
FIG. 3A is a cross sectional view of the vent plug and filter.

A vent hole 24, FIG. 2, is formed through floor 22 and communicably interconnects chamber 18 and a space 26 surrounded by annular base 15. Vent hole 24 receives a vent plug 28 to define a pressure equalizing or neutralizing vent in receptacle 12. As shown in FIG. 3, vent plug 28 includes a central channel 30 that extends fully through the vent plug. The channel accommodates an air filter 32. Vent plug 28 defines an air pressure equalizing vent that functions in the use of centrifuge tube assembly as described below. Alternative vent constructions formed unitarily with or separably from receptacle 12 may be utilized within the scope of this invention.

As shown in FIGS. 1 and 2, cap 36 is releasably engaged with open upper end 13 of receptacle 12. Cap 36 includes a generally cylindrical shape that conforms the cross sectional shape of the receptacle shown in FIG. 1A. The cap features an upper lid 38, FIGS. 1 and 2, having a circular shape that generally matches the circular cross sectional shape of the receptacle. An annular or cylindrical flange 40 is attached unitarily to and depends from lid 38. A conically tapered channel 42 is formed in the underside of flange 40. The flange is configured and sized such that it can be slid snugly and securely into interior chamber 18 of receptacle 12, as shown in FIG. 1. This effectively closes the receptacle so that it may be used in the manner disclosed herein. Lid 38 includes a peripheral lip 45, shown in FIG. 1, that interengages the peripheral notch 20 formed at upper end 13 of receptacle 12 when cap 36 is inserted into chamber 18. In this state, cap 36 is securely and snugly engaged with the receptacle. The interconnection is tight enough so that the cap remains in secure interengagement with the upper end of the receptacle during centrifuging of assembly 10 and subsequent fluid aspiration therefrom.

Conically tapered interior channel 42 of cap 36 is communicably connected with a single common inlet/outlet port 44 formed either unitarily or separately through lid 38 of cap 36. Port 44 includes a central opening that extends through lid 38. The upper end or stem 35, of port 44 is disposed exteriorly of a tubular receptacle, whereas the lower end of the inlet/outlet port communicates with the conically tapered channel 42. As a result, when cap 36 is interengaged with the open upper end 13 of receptacle 12, port 44 provides for exterior communication with the interior chamber 18 of receptacle 12.

A removable plastic closure 48 is preferably secured to the outer stem of port 44 by a connecting strap, not shown herein but see U.S. Pat. No. 7,976,796. During the centrifuging operation, as well as at other times when fluid is not being introduced into or removed from the tube, closure 48 is engaged with the upper exterior end of port 44 to maintain the port in a closed condition. The risks of fluid spillage and contamination are thereby reduced.

Although the receptacle is preferably formed with an open upper end interengaged by removable cap 36, in alternative embodiments, a permanently capped upper end may be utilized. Various alternative and/or analogous forms of construction for the upper end cap and common inlet/outlet port are disclosed in U.S. Pat. Nos. 6,835,353 and 7,976,796 the disclosures of which are incorporated herein by reference. Preferably cap 36 as well as inlet/outlet port 44 are likewise composed of polypropylene or other material similar to that forming the tubular receptacle itself. Normally, the common inlet/outlet port is molded together with the cap in a single manufacturing process. Associated types of integral and separated inlet/outlet ports may be utilized including Luer™ type ports as are described in U.S. Pat. Nos. 6,835,353 and 7,976,796.

As further shown in FIGS. 1 and 2, the exterior stem 35 of port 44 extends centrally from a threaded connection 46 that is formed unitarily on the upper surface of lid 38. Threads 46 are operably interengageable by complementary threads 52 formed interiorly on a removable tube cover 50. The removable cover has a generally circular cross sectional shape that corresponds to that of the centrifuge tube. In particular, cover 50 includes a cylindrical peripheral wall 54 and a flat top surface 56. When cap 36 is interengaged with receptacle 12 and cover 50 is threadably attached to cap 36, the flat top surface 56 allows the centrifuge tube assembly 10 to stand stably in an upright, inverted condition upon an underlying table or other flat surface. The flat top surface 56 also allows the assembly to be supported upright securely in an inverted condition within a standard centrifuge machine while the centrifuging operation is being performed. This is described more fully below. Cap 50 is preferably composed of a plastic or glass material similar to that comprising the other components of the assembly.

As previously described, a vent plug 28 is formed centrally through floor 22 of receptacle 12. This vent maintains a stable neutral pressure within tubular receptacle 12 during fluid injection and aspiration. It is critical that the vent be formed in the end of the tube opposite the capped end wherein the common inlet/outlet port is formed or otherwise in communication with a region of chamber 18 that does not communicate with port 44. This allows constituent separation and aspiration to be performed quickly and efficiently without the need for one or more aspiration pipes.

Figure 1A:
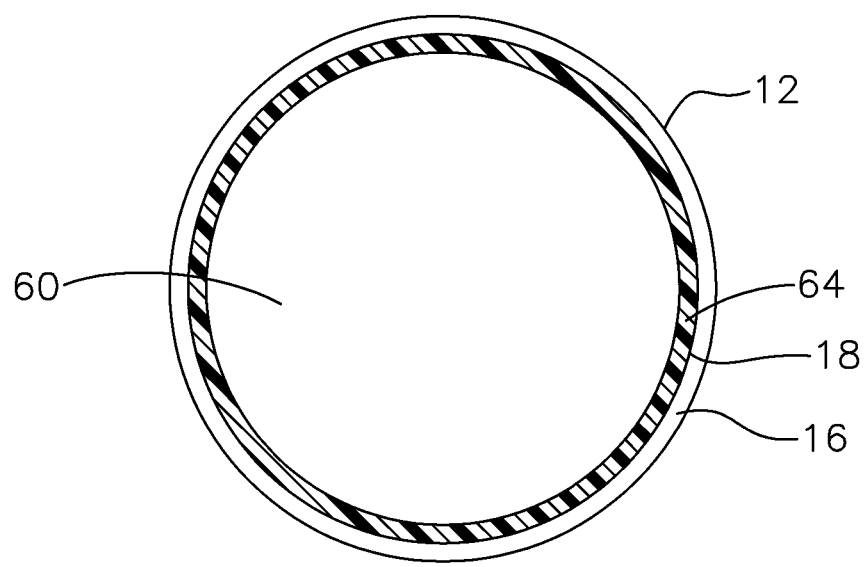
FIG. 1A is a cross sectional view taken along line 1A-1A of FIG. 1.

A liquid impermeable piston 60 is contained in chamber 18 and slidably mounted for longitudinal movement within chamber 18 of tubular receptacle 12. More particularly, as also shown in FIG. 1A, piston 60 has a generally circular, peripheral shape conforming to the interior shape of side wall 16. The piston features an annular peripheral groove 62. The groove accommodates an O-ring 64, which sealingly and slidably interengages the interior surface of side wall 16 of tubular receptacle 12. Piston 60 is movable longitudinally within chamber 18 of tubular receptacle 12 as indicated by doubleheaded arrow 63, FIG. 1. The upper surface 66 of piston 60 has a concave shape. The bottom surface 67 of piston 60 includes a central recess 69 that receives the upper interior end of vent plug 28 when piston 60 is pushed to its lowest position within chamber 18 during operation of assembly 10, as described below.

Prior to usage of assembly 10, sealing piston 60 is typically positioned within chamber 18 of receptacle 12 proximate the upper end 13 of the receptacle Cap 36 is engaged with receptacle 12 as previously described and closure 48 is engaged with inlet/outlet port 44 so that the interior chamber 18 of receptacle 12 is closed. Cover 50 may also be attached to the cap in order to further isolate and enclose chamber 18 and to reduce the risk of fluid contamination during use of assembly 10.

Figure 4:
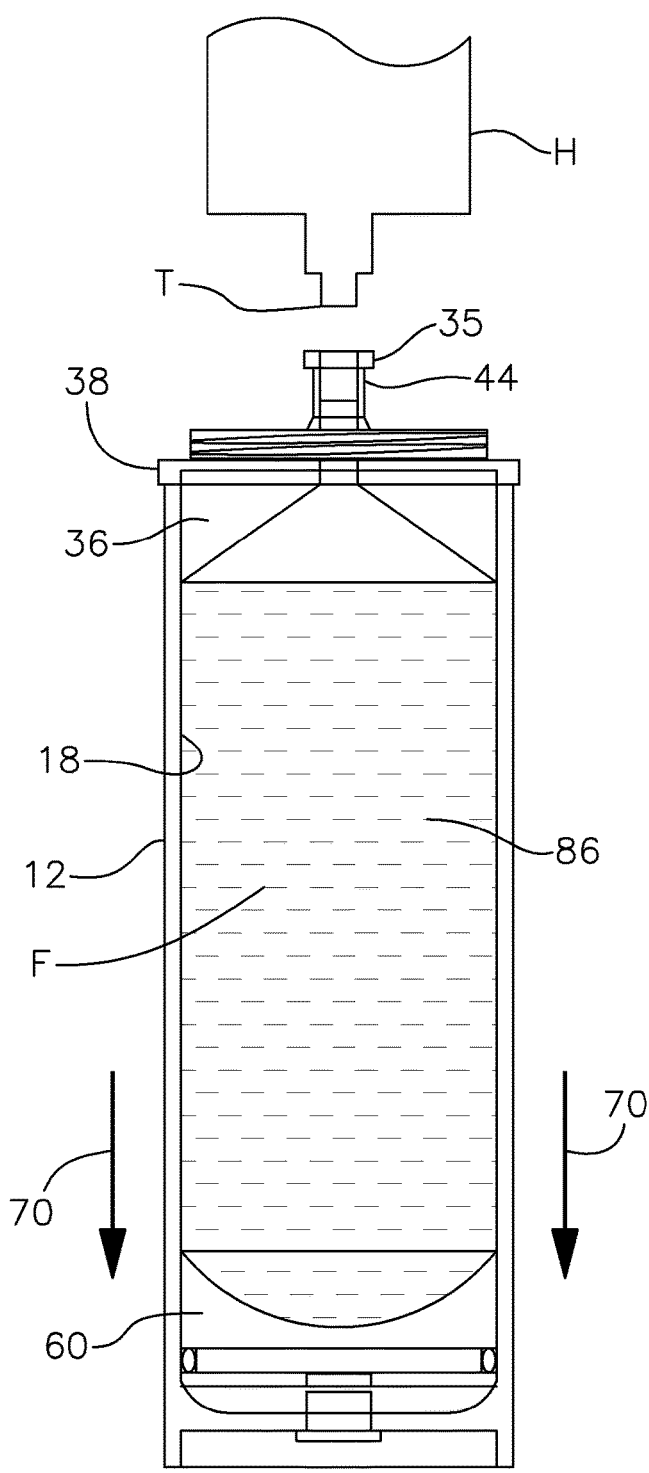
FIG. 4 is a view similar to FIG. 1 with the cover and port closure removed and a hypodermic syringe positioned for operably engaging the receptacle; a biological fluid to be separated is depicted in the tubular receptacle.
Figure 5:
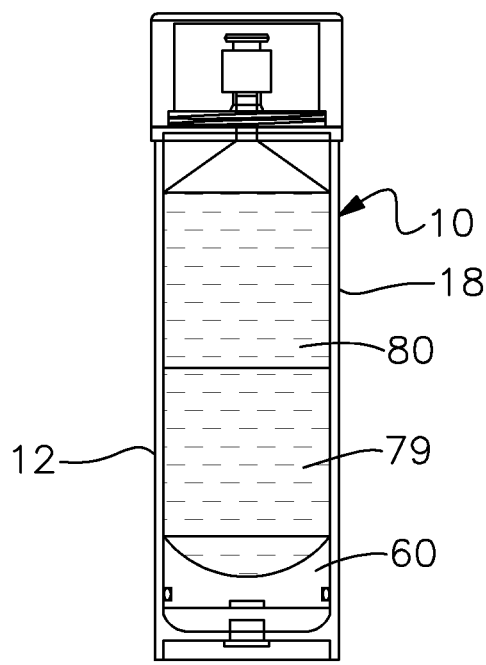
FIG. 5 is a view similar to FIG. 1 wherein the tube has been centrifuged to separate a blood product in the tube into two constituent components; namely red blood cells and plasma, with the plasma layer positioned so that it can be aspirated from the tube first.
Figure 6:
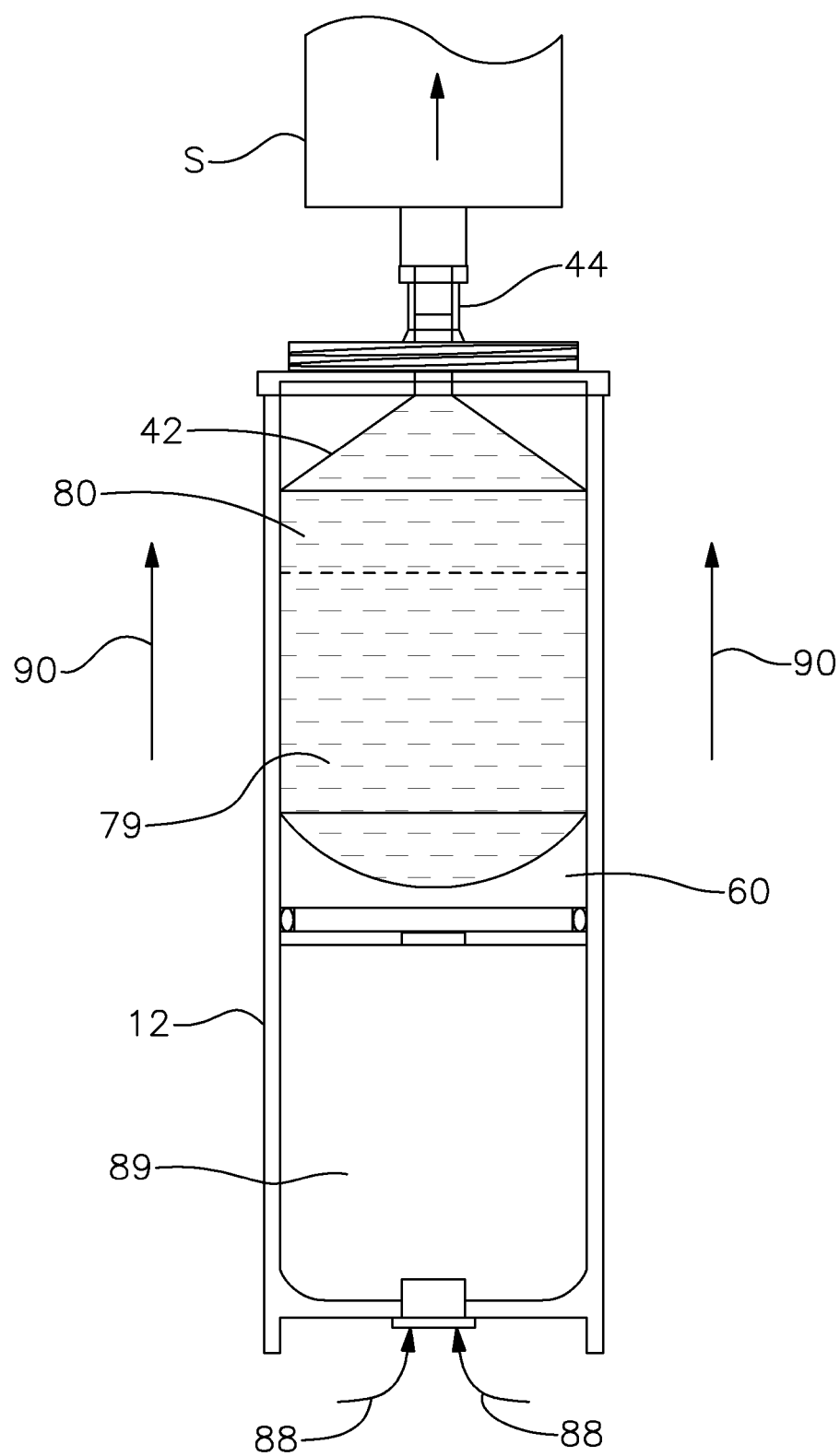
FIG. 6 is a view similar to FIG. 4 wherein a hypodermic syringe engaged with the tube is being operated to aspirate successive constituent components of the biological product from the tube.

Assembly 10 is utilized to centrifuge a biological product into its constituent components and then to aspirate one or more of those components as shown in FIGS. 4-6. A preferred representative use for centrifuge tube assembly 10 is the separation of a blood sample into constituent blood components. Typically, it is desirable to separate platelets and/or plasma from red blood cells such that a platelet-rich blood product may be used in various surgical, medical or veterinary applications. This process is performed in the following manner using assembly 10. Initially, the empty receptacle 12 is stood upright on an underlying table T with on its base 15 supporting the assembly upon the table as shown in FIG. 1. Cover 50 is disengaged from cap 36 and closure 48 is removed from port 44. Blood product F (or an alternative fluid biological product) is then added to receptacle 12 as depicted in FIG. 4. Specifically, a hypodermic syringe H carrying the blood or other biological product is operably engaged with upper stem 35 of inlet/outlet port 44. The tip T of hypodermic syringe H may be engaged with port 44 in a conventional manner. See U.S. Pat. Nos. 6,835,353 and 7,976,796. Exterior stem 35 holds dispensing tip T securely in place so that the hypodermic syringe is securely engaged with assembly 10. The syringe is then operated in a conventional manner to inject and introduce the product to be separated through port 44 and into the interior chamber 18 of receptacle 12. More particularly, blood product or other biological product F (e.g. bone marrow) is transmitted through port 44 into the upper space or region 86 of chamber 18 located between cap 36 and piston 60. As biological product F is introduced into space 86, the increasing volume and pressure of fluid product F in region 86 drives piston 60 downwardly, as indicated by arrows 70. Blood product is injected into the receptacle by syringe H in this manner until the desired volume of fluid is added to chamber 18. Vent plug 28 allows air within a region 89 of the chamber between the descending piston and the lower end 14 of receptacle 12 to escape from the chamber through the vent plug so that the air pressure in the receptacle is neutralized. As the piston is pushed downwardly through chamber 18 by the increasing volume of fluid F, the peripheral O-ring 64 of piston 60 remains in sealing engagement with the interior side wall surface of receptacle 12 so that chamber regions 86 and 89 remain separated from one another. No fluid enters region 89 below piston 60. When the selected amount of fluid has been added to the receptacle, hypodermic syringe H is disengaged from assembly 10. For human blood work, the selected volume of blood may be, for example, 50 ml. This volume is preferred because it typically yields approximately 5 ml of platelet-rich blood product. Other volumes may be used as required by particular applications.

After the desired amount of blood product or other fluid biological product is introduced into the tubular receptacle, syringe H is disengaged from port 44 and closure 48 is reengaged with the port. Tubular receptacle 12 is then placed in a conventional centrifuge, either by itself or with other fluid filled tubular assemblies in accordance with this invention. Again, base 15 supports receptacle 12 in a stable, upright condition in the centrifuge machine. The loaded centrifuge is operated in an established manner for a selected time (e.g. preferably 5-7 minutes) in order to separate the constituent components of blood or other fluid sample F. Various known types of centrifuge machines may be employed for this task. A single round or multiple rounds of centrifuging may be utilized so that the selected biological product F is separated into two or more constituent components as are required for a particular application.

After centrifuging is complete, FIG. 5, assembly 10 is removed from the centrifuge and supported by its annular base 15 on the table or other support surface. In cases where fluid sample F comprises a blood sample, the centrifuged sample may appear as shown therein. Specifically, centrifuging causes the red blood cells 79 to collect in a dark red layer proximate the bottom of receptacle 12 and immediately adjacent piston 60. A discrete layer of plasma 80 exhibiting a yellow color is formed in the upper region of chamber 18 above red blood cells 79. In alternative centrifuging applications, an intermediate layer of platelets in the form of a white "buffy" coat may be disposed between the plasma and red blood cells layers. In embodiments when other fluid biological products are centrifuged, two or more discrete constituent component layers are formed in an analogous manner within the receptacle chamber above the piston. In all cases, piston 60 remains in sealing interengagement with the interior wall of receptacle 12 such that the separated biological constituents are maintained securely within chamber 18 above the piston. Indeed, during the centrifuging process, the diameter of the O-ring typically expands somewhat to provide an even more securing sealing interengagement with the interior cylindrical wall of the receptacle.

The user next aspirates one or more layers of the sequestered constituent components from the centrifuged fluid. This is accomplished by engaging one or more aspirating syringes S with assembly 10 in the manner shown in FIG. 6. For the blood product example that has been described herein, the user typically wishes to first aspirate plasma/platelets using a syringe S. Initially, the user removes closure 48, FIG. 1 and engages the syringe with port 44. The syringe is operated to aspirate the upper layer of plasma 80 from the chamber 18 through conical channel 42 and port 44. Plasma is drawn through the common inlet/outlet port and into a respective syringe. As fluid F is removed from the tubular receptacle, vent plug 28 allows air to be pulled or drawn into lower region 89 of chamber 18 as indicated by arrow 88. Again pressure within receptacle 12 is neutralized, a vacuum within lower chamber region 89 is avoided and piston 60 is driven upwardly as indicated by arrows 90 in FIG. 6. Concave surface 66 of piston 60 enables the piston to better maintain a fluid-tight seal so that intermixing and cross contamination of the separated constituents are minimized. Conical channel 42 facilitates and improves removal and collection of the plasma/platelets 80 during aspiration.

After the plasma is completely removed, the user may replace the first syringe, which has been used to remove the plasma, with a second syringe designed to aspirate red blood cells. Aspiration may continue using the new syringe to remove red blood cells 79 through port 44. Piston 60 continues to be driven upwardly within tubular chamber 18 while maintaining sealing interengagement with the interior side wall of the tubular receptacle. Three constituent layers (plasma, platelets and red blood cells) and other biological products may be analogously aspirated in a sequential manner following centrifugation. Platelets plasma, bone marrow aspirate and other fluid constituent can thereby be effectively sequestered, retrieved and utilized as needed for surgical/wound care procedures. After aspiration is completed, the remaining (unaspirated) red blood cells within the assembly and assembly 10 itself may be disposed of in a medically acceptable manner.

During the foregoing process, filter 32 in vent plug effectively restricts particles and bioburdens from entering chamber 18 through the vent. This reduces the risk of contamination of the fluid during injection and aspiration.

Although the foregoing example depicts the use of centrifuge tube assembly in connection with the separation and aspiration of constituent blood components, it should be understood that the tube may be used equally effectively to separate and aspirate a wide variety of alternative biological products. These include stem cells, bone marrow aspirate and various other fluids/chemicals.

The centrifuge tube disposed here may be employed in a wide variety of medical, biomedical, veterinary and other types of procedures. When veterinary blood work is involved, the tube will typically comprise a much larger volume that is utilized during human blood work.

The devices and processes described above are particularly effective in allowing a blood sample to be conveniently separated into discrete blood products, which may then be sequentially aspirated or removed so that a platelet-rich product is conveniently obtained. This entire procedure is performed without excessive mixing or cross-contamination of the individual components. The separation process is performed more quickly, inexpensively, efficiently and effectively then has hereto been possible using known centrifuge tubes. The present device is especially advantageous due to its use of relatively few working parts. Manufacturing the assembly is thereby facilitated and its attendant cost is reduced considerably. By the same token, the centrifuge and aspiration process is performed much more quickly and easily then is accomplished using conventional products, including the apparatus of U.S. Pat. No. 7,179,391 for example.

The centrifuge tube assembly of the present invention improves the manufacture of centrifuge tubes used for the purposes described herein. In particular, the present invention totally eliminates the need to use aspirating pipes within the centrifuge tube. This greatly simplifies and reduces the expense of manufacturing such products. Moreover, both aspiration and injection may be performed more quickly and reliably without aspiration pipes. To eliminate these components, it is a critical that a pressure neutralizing vent and inlet/outlet port must communicate with respective regions of the centrifuge tube chamber separated by (i.e. located on opposite sides of) the sealing piston or diaphragm. In this way, fluids may be injected into and aspirated from the tube chamber directly through a common inlet/outlet port and without the need for a separate aspirating pipe attached to the inlet/outlet port and extending through the piston or diaphragm. The present invention also eliminates problems that can often occur from the use of aspirating pipes, namely kinking or the pipe and resulting malfunction of the tube.

It should be understood that other variations and modification of the centrifuge tube assembly may be employed within the scope of this invention. The terms "upper end" and "lower end" may be used interchangeably and should be construed broadly to refer to the respective ends or locations proximate the respective ends of the tube as indicated, for example, in the alternative orientations shown in FIGS. 5 and 7 respectively.

Figure 7:
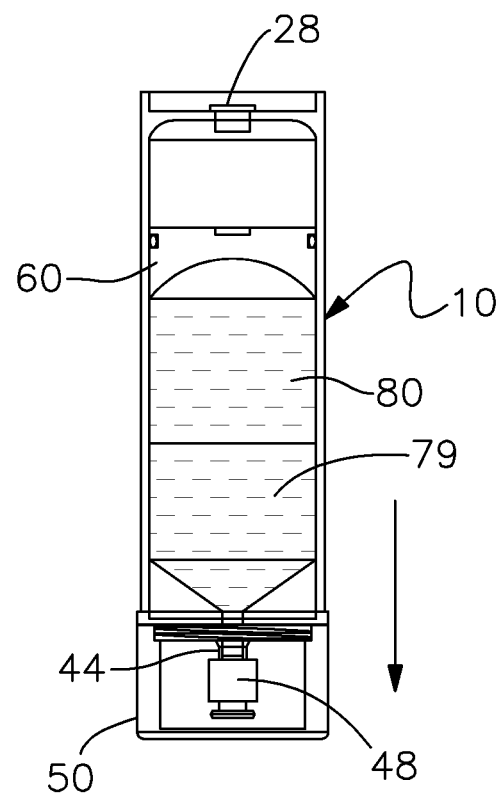
FIG. 7 is a view similar to FIG. 5 with the tube inverted so that the centrifuged blood product is oriented in layers that permit red blood cells to be aspirated from the tube first.

In the alternative version shown in FIG. 7, tube 10 may be employed to aspirate red blood cells first. In particular, the blood product is initially added as previously shown in FIG. 4. Assembly 10 is then inverted as shown in FIG. 7 so that the vent plug 28 is positioned at the top end and the inlet/outlet port 44 is positioned at the lower end of the tube. In this orientation, tube 10 is placed into the centrifuge machine. As previously indicated, the attached cover 50 includes a flat top surface that allows the inverted assembly to sit stably within the centrifuge machine. Centrifuging is then performed in accordance with the selected manner so that the constituent components of the fluid product, namely red blood cells 79 and plasma 80 are again separated as shown in FIG. 7. In this example, the red blood cells constitute the lower layer of the centrifuge fluid, and because the assembly has been inverted, the red blood cells 79 are adjacent to the inlet/outlet port 44. After centrifuging is completed, cap 50 is removed, closure 48 is disengaged from port 44 and a hypodermic needle is engaged with the inlet/outlet port so that red blood cells may be aspirated first from the centrifuge tube assembly. As in the previously described embodiment, vent plug 28 neutralizes or equalizes the air pressure within the receptacle so that the piston 60 is drawn upwardly during aspiration to facilitate removal initially of the red blood cells 79, and subsequently the plasma 80 from the receptacle.

It should be further understood that the centrifuge tube assemblies of this invention may be employed to separate various other types of biological products, fluids and chemicals. Likewise, in such applications the individual components may be sequestered and removed quickly and conveniently without undue mixing and cross-contamination.

In still other versions of this invention, the inlet/outlet port and vent may be installed in alternative locations of the receptacle in communication with the upper and lower chamber regions respectively. These may include alternative locations in the side wall or elsewhere. In all versions, the piston must separate and isolate the upper and lower chamber regions from one another so that the inlet/outlet port and the vent communicate with different respective chamber regions, fluid is sequestered in the upper chamber region and the assembly thereby operates effectively without the need for aspirating pipes.

From the foregoing it may be seen that the apparatus of this invention provides for a centrifuge tube, which enables biological products such as blood, stem cells, bone marrow aspirate and the like to be effectively separated into constituent components and aspirated after the biological product has been centrifuged. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

Other embodiments will occur to those skilled in the art and are within the following claims:

What is claimed is:

1. A centrifuge tube assembly for separating and aspirating constituent components of a fluid biological product, said assembly comprising:

an elongate receptacle having an interior chamber for receiving the fluid biological product therein, said receptacle having a lower end and a side wall that extends upwardly from said lower end;

a cap engaging said side wall and extending across an upper end of said receptacle;

a common inlet and outlet port formed in one of said cap and said receptacle, said common inlet and outlet port configured for injecting the fluid biological product into said chamber and aspirating the constituent components from said chamber after the constituent components are separated from the fluid biological product;

a vent formed through said lower end of said receptacle; and a piston mounted within said chamber and being slidable through said chamber while maintaining sealing engagement with an interior surface of said side wall of said receptacle; the fluid biological product being injected through said common port into a region of said chamber between said piston and said upper end of said receptacle and said receptacle being centrifuged to separate the fluid product into constituent components thereof, which components are disposed in respective fluid layers in said chamber, whereby one or more of the fluid layers may be aspirated through said common inlet and outlet port, said vent neutralizing pressure within said receptacle chamber as fluid is injected into said chamber and as constituent components are aspirated from said chamber through said common inlet and outlet port; said piston consisting of a cylindrical element having a generally circular peripheral shape conforming to the interior shape of the side wall of said receptacle, said piston being driven toward said lower end of said receptacle exclusively in response to hydraulic pressure exerted by fluid biological product injected into said chamber and toward said upper end of said receptacle exclusively in response to suction created in said chamber by aspiration of the constituent components from said chamber.

2. The assembly of claim 1 in which said cap is removably attached to said side wall of said receptacle.

3. The assembly of claim 1 in which said lower end of said receptacle carries an annular base for supporting said receptacle to extend upwardly from an underlying supportive surface, said vent being formed through said lower end of said receptacle interiorly of said annular base.

4. The assembly of claim 1 further including a closure that is removably attached to said common inlet and outlet port outside of said chamber for selectively opening said port to permit introduction of the fluid biological product into said chamber and aspiration of a separated constituent component therefrom and closing said port while said receptacle is being centrifuged.

5. The assembly of claim 1 in which said vent maintains a neutral air pressure within a region of said chamber between said piston and said lower end of said receptacle to permit said piston to slide toward said lower end when fluid biological product is injected into said receptacle and toward said upper end when a constituent component is aspirated from said receptacle.

6. The assembly of claim 1 in which said piston carries an O-ring that sealingly interengages said interior surface of said side wall.

7. The assembly of claim 1 in which said piston includes a concave face directed toward said region of said chamber between said piston and said cap.

8. The assembly of claim 1 in which said cap includes a tapered channel that communicates with said common inlet and outlet port for facilitating aspiration of the one or more fluid layers.

9. The assembly of claim 1 in which said vent includes a vent plug received in a vent hole formed through said lower section, said vent plug carrying a filter for restricting the entry of contaminants into said chamber through said vent.

10. The assembly of claim 1 further including a cover that is removably interengageable with said receptacle for selectively enclosing an exterior section of said common inlet and outlet port.

11. The assembly of claim 10 in which said cover includes a flat top surface for slidably supporting said receptacle in an inverted condition for centrifuging.

12. The assembly of claim 1 in which said common inlet and outlet port includes a Luer™ port.

13. A method of separating fluid biological product into constituent components using a centrifuge assembly, which includes a receptacle having upper and lower ends and a side wall that extends between said upper and lower ends, a common inlet and outlet port formed in said upper end of the receptacle and configured for injecting fluid biological product into said receptacle and aspirating constituent components from said receptacle, a vent formed through said lower end and a piston mounted for sliding within the receptacle while maintaining sealing engagement with the side wall of thereof, said method comprising:
  injecting the fluid biological product into the receptacle through the common port into a region of the chamber between the piston and the upper end of the receptacle such that the hydraulic pressure of the injected fluid drives said piston downwardly through the receptacle and until said receptacle is filled to a selected level by the biological product;
  closing said common inlet and outlet port;
  centrifuging said receptacle to separate the fluid biological product into constituent components;
  opening said common inlet and outlet port; and
  aspirating one or more of the constituent components from said receptacle chamber through said common inlet and outlet port such that a suction is generated in said receptacle chamber and said sealing piston is drawn upwardly through said receptacle, said vent neutralizing pressure within said receptacle chamber as fluid is introduced into said chamber and as constituent components are aspirated from said chamber.

14. The method of claim 13 in which s common inlet and outlet port includes a Luer™ port through which biological product is injected and constituent components are aspirated.

* * * * *